United States Patent [19]

Postle et al.

[11] Patent Number: 4,609,620
[45] Date of Patent: Sep. 2, 1986

[54] PYRAZOLONE COMPOUNDS AND A PROCESS FOR THEIR MANUFACTURE

[75] Inventors: Stephen R. Postle; William E. Long, both of Wilmslow, England

[73] Assignee: Ciba Geigy AG, Basel, Switzerland

[21] Appl. No.: 721,348

[22] Filed: Apr. 9, 1985

Related U.S. Application Data

[63] Continuation-in-part of Ser. No. 471,954, Mar. 3, 1983, abandoned.

[30] Foreign Application Priority Data

Mar. 11, 1982 [GB] United Kingdom ............... 8207068

[51] Int. Cl.⁴ .................................................. G03C 7/32
[52] U.S. Cl. ..................................... 430/554; 430/505; 430/555
[58] Field of Search .................... 430/554, 505, 555

[56] References Cited

U.S. PATENT DOCUMENTS 3,311,476 3/1967 Loria ..................................... 430/555
3,419,391 12/1968 Young ................................... 430/555
4,076,533 2/1978 Ota et al. .............................. 430/555
4,273,861 6/1981 Shiba et al. ........................... 430/554
4,366,237 12/1982 Ichijima et al. ....................... 430/554

Primary Examiner—Mary F. Downey
Attorney, Agent, or Firm—Joseph G. Kolodny

[57] ABSTRACT

Compounds of the formula

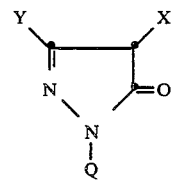

where Y is a tertiary group, X is hydrogen or a leaving group, and Q is hydrogen, amidino, alkyl or aryl, there being present in Y or Q a ballasting group which comprises 10 to 30 carbon atoms, exhibit a high secondary absorption in the blue region of the visible spectrum and are useful couplers in chromogenic monochrome negative material.

1 Claim, No Drawings

PYRAZOLONE COMPOUNDS AND A PROCESS FOR THEIR MANUFACTURE

This is a continuation-in-part application of the copending application Ser. No. 471,954, filed Mar. 3, 1983, now abandoned.

Substituted pyrazolone compounds which are used as colour couplers in colour photographic materials have long been known. These compounds are useful as the magenta coupling components in tri-pack colour photographic materials.

Use of pyrazolone compounds in the photographic field is described for example in "the Theory of the Photographic Process" 4th edn.ed.. T. H. James. p. 356–358. However most of these pyrazolone compounds are difficult and expensive to manufacture, because of the need to incorporate into the pyrazolone molecule the features giving good colour absorption to the dye produced by coupler.

Recently, there has been interest in photographic materials which comprise mixtures of colour couplers to give monochrome images, for example as described in European Patent application No. 25,775. In such materials it is no longer necessary for the dyes produced from each coupler to have the single sharp absorption maximum necessary in colour negatives. Thus we have found new pyrazolone compounds which have a high secondary absorption in the blue region of the visible spectrum which are useful in chromogenic monochrome negative material, moreover they are easy and cheap to manufacture. Use of these compounds in chromogenic monochrome materials results in useful economies, not only because of the easy synthesis of these compounds, but also because of the reduction of the coating weight of the yellow coupler present in the assembly to give an overall neutral density.

According to the present invention there is provided a pyrazolone compound having a high secondary absorption in the blue region of the visible spectrum, which is at least 54% of the primary absorption, said pyrazolone dye being of the formula

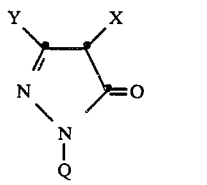

(1)

where Y is —$CR_1R_2R_3$, wherein $R_1$, $R_2$ and $R_3$ are each independently alkyl, aryl, aralkyl or alkaryl which groups are unsubstituted or substituted, or two or three of the groups $R_1$, $R_2$ and $R_3$ form a 5- or 6-membered monocylic or polycylic ring system which is unsubstituted or substituted, X is hydrogen or a leaving group and Q is hydrogen, amidino, alkyl or aryl which groups are unsubstituted or substituted, there being present in Y or Q a ballasting group which comprises 10 to 30 atoms.

Further objects of the present invention are a process for the preparation of these pyrazolone compounds and a photographic material containing these compounds.

Y in the compounds of the formula (1) is a tertiary group of the formula

Independently from one another, $R_1$, $R_2$ and $R_3$ are alkyl, aryl, aralkyl or alkaryl. These groups may be further substituted. Preferred alkyl groups are long chain alkyl groups, preferably having 10 to 20 carbon atoms such as decyl, dodecyl, hexadecyl, octadecyl, nonadecyl and eicosyl as well as isomers thereof. These long chain alkyl groups act as a ballasting group and preferably one of $R_1$, $R_2$ and $R_3$ represents a ballasting alkyl group.

It is also possible that $R_1$, $R_2$ or $R_3$ represents a group which comprises a ballasting group. Such groups are preferably of the formula

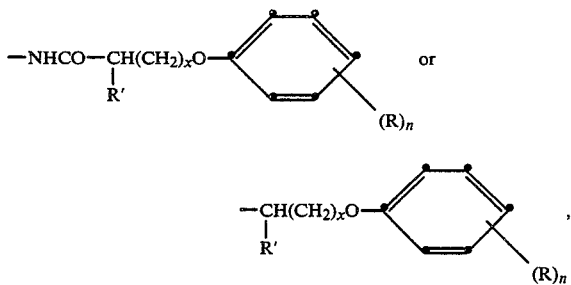

wherein R is alkyl having 1 to 20 carbon atoms, R' is alkyl having 1 to 4 carbon atoms, x is 0, 1 or 2, and n is 1 or 2. Preferably, if n is 1, R is a long chain alkyl group of 10 to 20 carbon atoms, pentadecyl e.g., and, if n is 2, R is preferably alkyl having up to 10 carbon atoms such as t-amyl. Another group which comprises a ballasting group is a substituted phenyl radical such as long chain alkyl or thioalkyl substituted phenyl, where the alkyl moieties contain preferably 10 to 20 carbon atoms. If $R_1$, $R_2$ and $R_3$ are a non-ballasting alkyl group, then this alkyl group preferably comprises 1 to 10 and, more preferably 1 to 5 carbon atoms such as methyl, ethyl, propyl, butyl or pentyl. Suitable aryl groups $R_1$, $R_2$ and $R_3$ are phenyl, and naphthyl, e.g. Benzyl, phenylethyl and benzhydryl are preferred aralkyl radicals $R_1$, $R_2$ and $R_3$. In the meaning of alkaryl, $R_1$, $R_2$ and $R_3$ preferably represent a phenyl radical which is substituted by preferably 1 or 2 alkyl groups which has (have each) 1 to 10 carbon atoms, such as methyl, propyl, butyl, pentyl, octyl and decyl as well as isomers thereof. Further substituents on these groups $R_1$, $R_2$ and $R_3$ comprise alkyl, aryl, alkoxy, aryloxy, alkylthio, arylthio, alkylsulphonyl, arylsulphonyl, where the alkyl moieties preferably contain 1 to 6 carbon atoms and aryl preferably denotes phenyl, (carboxylic) ester, preferably alkyl ester, having 1 to 4 carbon atoms in the alkyl group or amide, sulphonamido and halogen such as chlorine or bromine. Two of $R_1$, $R_2$ and $R_3$ or all of $R_1$, $R_2$ and $R_3$ form ring systems which are mono- or polycyclic. Preferably, these ring systems contain 5 or 6 ring atoms (per ring), preferably carbon atoms, and are e.g. cyclopentyl and cyclohexyl which may be further substituted by alkyl groups such as methyl, propyl, i-propyl, butyl or t-butyl. Preferred polycyclic ring systems contain 2 or 3, preferably saturated rings and are e.g. decalinyl, tetradecahydrophenanthrenyl, tetradecahydroanthracenyl, adamantyl, bicycloheptyl and camphanyl. These ring systems may also be further substituted by alkyl groups preferably each having 1 to 4 carbon atoms such as methyl or i-propyl. Such systems also act as ballasting groups.

X is hydrogen or a leaving group which leaves the pyrazolone ring system when coupling with the oxidation product of a developing agent. Suitable leaving groups are essentially those which are commonly used in photographic colour couplers, e.g. 5- or 6-membered heterocyclic rings of the formula

W represents the non-metallic atoms necessary to complete the ring system which may be further substituted by alkyl, aryl, alkoxy, aryloxy, where the alkyl moieties preferably contain 1 to 4 carbon atoms and aryl preferably denotes phenyl, or by carboxylic acid or amido groups. Suitable ring systems are e.g. imidazole, pyrazole, triazole and dimethylimidazol. Other suitable leaving groups are $-SR_5$, $-OR_5$ and $-OCOR_5$, where $R_5$ is alkyl, preferably having 1 to 10 carbon atoms, aryl, preferably phenyl, or a heterocyclic system such as triazole or tetrazole, which systems may be further substituted by alkyl having preferably 1 to 5 carbon atoms. The alkyl and aryl groups $R_5$ may be further substituted by aryl, alkoxy, aryloxy, alkylthio, arylthio, alkylsulphonyl, arylsulphonyl where the alkyl moieties preferably contain 1 to 6 carbon atoms and aryl preferably denotes phenyl; (carboxylic) ester preferably alkyl ester, having 1 to 4 carbon atoms in the alkyl group or amide, sulphonamide or halogen such as chlorine or bromine.

The alkyl group Q preferably contains 1 to 20 carbon atoms. Suitable alkyl groups are mentioned above in the explanations of $R_5$ and Y, for example. Q denotes further an amidino group

Preferably, Q is a substituted aryl group of the formula

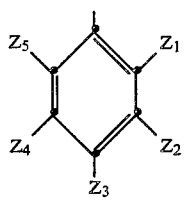

where $Z_1$ to $Z_5$ are each hydrogen, halogen, preferably chlorine or bromine, or $-OR_4$, $-NHCOR_4$, $-CONHR_4$, $-SO_2NHR_4$, $-COOR_4$, $-NHCOOR_4$, $-SR_4$ or $-SO_2R_4$, where $R_4$ represents alkyl or aryl which groups are unsubstituted or substituted. Preferably, $R_4$ denotes those alkyl, aryl and also ballasting groups which are mentioned above for $R_1$, $R_2$ and $R_3$.

Most preferably Q is the group of the formula

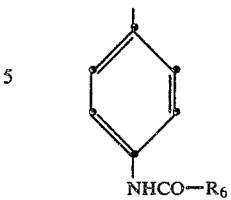

where $R_6$ is a ballasting group containing 10 to 30 carbon atoms. $R_6$ is preferably a ballasting alkyl group containing 10 to 20 carbon atoms or $R_6$ is a group of the formula

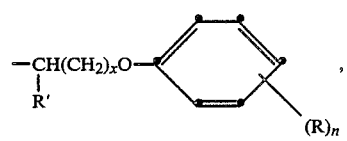

where R, R', n and x are as defined above.

As stated there must be present either in the group Q or the group Y a ballasting group containing at least ten carbon atoms. This is to render the coupler and the dye formed therefrom substantive to the photographic layer in which it was coated, and to give oil solubility to the coupler. A particularly suitable ballasting group is the di-tert-amylphenoxy group.

The high secondary density of the dyes formed by the couplers of the present invention is believed to be caused by the presence of the tertiary substituent Y in the 3-position of the pyrazolone ring.

In suitable compounds of the formula (1) $R_1$, $R_2$ and $R_3$ are each independently alkyl having 1 to 20 carbon atoms, phenyl, naphthyl, benzyl, phenylethyl, benzhydryl or phenyl substituted by 1 or 2 alkyl groups each having 1 to 10 carbon atoms, these radicals being unsubstituted or substituted by alkyl, aryl, alkoxy, aryloxy, alkylthio, arylthio, alkylsulphonyl, arylsulphonyl, carboxylic ester or amide, sulphonamido or halogen.

Preferably, $R_1$, $R_2$ and $R_3$ are each independently unsubstituted or substituted by alkyl alkoxy, alkylthio or alkylsulphonyl, the alkyl moieties each having 1 to 6 carbon atoms, phenyl, phenoxy, phenylthio, phenylsulphonyl, carboxylic alkyl ester having 1 to 4 carbon atoms in the alkyl moiety, carboxylic amide, sulphonamido, chlorine or bromine.

More preferably, $R_1$, $R_2$ and $R_3$ are each independently alkyl having 1 to 6 carbon atoms which is unsubstituted or substituted by a carboxylic alkyl ester having 1 to 4 carbon atoms in the alkyl moiety.

$R_1$, $R_2$ and $R_3$, each being methyl, is particularly preferred.

In another group of suitable compounds of the formula (1) two of $R_1$, $R_2$ and $R_3$ form a cyclopentyl or cyclohexyl ring or $R_1$, $R_2$ and $R_3$ form a decalinyl, tetradecahydro-phenanthrenyl or -anthracenyl, adamantyl, bicycloheptyl or camphanyl system, these rings and systems being unsubstituted or substituted by alkyl having 1 to 4 carbon atoms.

Preferably, $R_1$, $R_2$ and $R_3$ form a tetrahydrophenanthrenyl or adamantyl system.

Preferred compounds of the formula (1) contain a leaving group which is selected from hydrogen or a 5- or 6-membered heterocyclic ring of the formula

where W represents the non-metallic atoms necessary to complete an imidazole, pyrazole or triazole ring, which is unsubstituted or substituted by alkyl or alkoxy each having 1 to 4 carbon atoms, phenyl, phenoxy, carboxylic acid or amido, or X is —SR$_5$, —OR$_5$ —O-COR$_5$, where R$_5$ is alkyl having 1 to 10 carbon atoms, phenyl or triazolyl or tetrazolyl which are unsubstituted or substituted by alkyl having 1 to 5 carbon atoms, the alkyl or phenyl groups R$_5$ being unsubstituted or substituted by alkoxy, alkylthio- or alkylsulphonyl, the alkyl moieties containing each 1 to 6 carbon atoms, phenyl, phenoxy, phenylthio, phenylsulphonyl, carboxylic alkyl ester having 1 to 4 carbon atoms in the alkyl moiety, carboxylic amide, sulphonamide, chlorine or bromine.

More suitable leaving groups are hydrogen, imidazolyl, dimethylimidazolyl, pyrazolyl, triazolyl, —SR$_5$ or —OR$_5$, where R$_5$ is alkyl having 1 to 10 carbon atoms, phenyl, triazolyl or tetrazolyl.

The compounds of the formula (1) exhibit particularly good properties, when Q is hydrogen, amidino, alkyl having 1 to 20 carbon atoms or phenyl of the formula

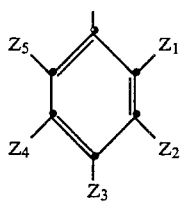

where Z$_1$ to Z$_5$ are each hydrogen, halogen, —OR$_4$, —NHCOR$_4$, —CONHR$_4$, —SO$_2$NHR$_4$, —COOR$_4$, —NHCOOR$_4$, —SR$_4$ or —SO$_2$R$_4$, where R$_4$ is alkyl or aryl which is unsubstituted or substituted.

More preferably, R$_4$ is alkyl having 1 to 20 carbon atoms or phenyl which is unsubstituted or substituted by 1 or 2 alkyl groups each having 1 to 10 carbon atoms.

Particularly preferred substituents Q are a group of the formula

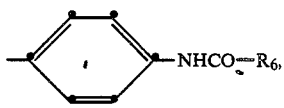

where R$_6$ is a ballasting alkyl group containing 10 to 20 carbon atoms or is a group of the formula

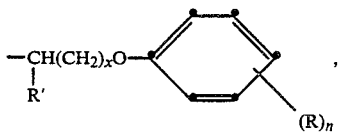

where R is alkyl having 1 to 20 carbon atoms, R' is alkyl having 1 to 4 carbon atoms, x is 0, 1 or 2 and n is 1 or 2.

Examples of particularly useful of the formula (1) are those of the formulae (2) to (10):

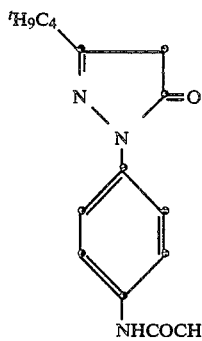

(2)

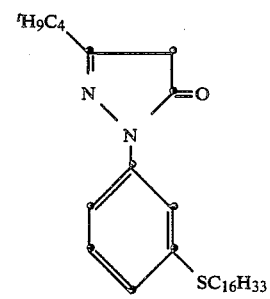

(3)

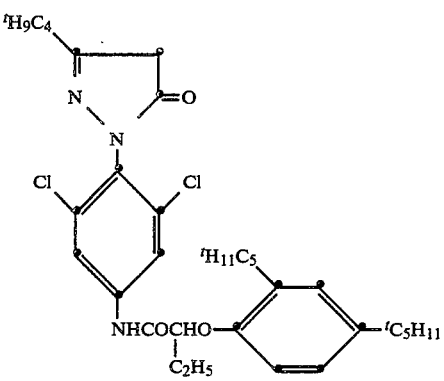

(4)

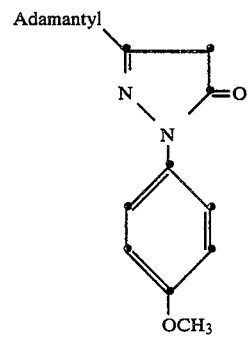

(5)

-continued (6) 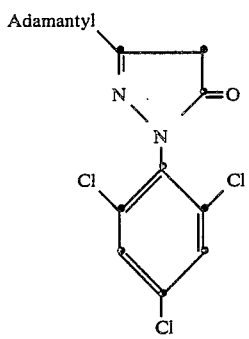

(7) 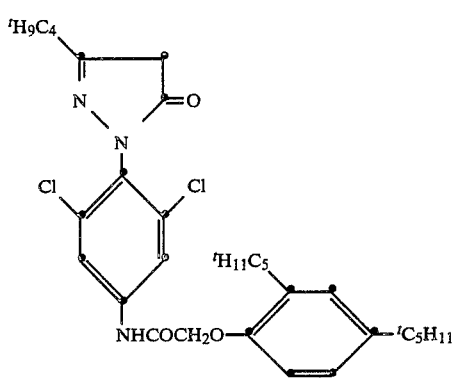

(8) 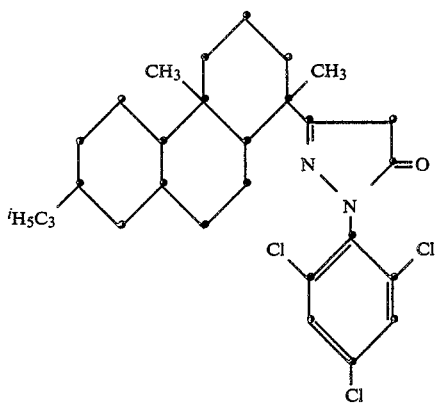

(9) 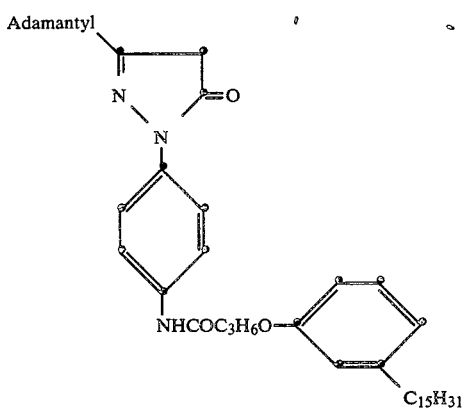

-continued

(10) 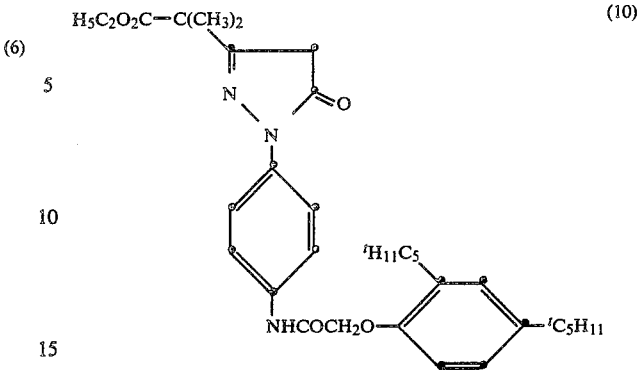

Compounds of formula (1) are prepared by reacting a substituted keto acetic ester of the formula

where X and Y have the meanings assigned above and $R_6$ is alkyl or aryl with a substituted hydrazine of the formula

where Q has the meaning assigned above.

This reaction may be carried out neat or in a suitable solvent, without catalyst, or with an acidic or basic catalyst, at temperatures of 20° C. up to the boiling point of the reaction mixture. A particularly suitable solvent is ethanol together with an acetic acid catalyst and at reflux temperature.

Alternatively and additionally the condensation of the keto ester of formula (11) and the hydrazine of formula (12) may be facilitated if certain of the substituent groups are present in protected forms. An example is the protection of a hydroxyl group as an ester during the condensation with subsequent liberation of the free hydroxyl group. A further modification is, for example, the presence of a nitro group during the condensation, which can subsequently be reduced and reacted to form amide or sulphonamide groups.

The coulour photographic material of the present invention is of particular use as chromogenic monochrome film material wherein after imagewise exposure and colour development the dye formed from the colour coupler or couplers present in the material form a monochrome image from which black and white prints may be obtained.

When the photographic silver halide material of the present invention after imagewise exposure is processed to form a dye image from the pyrazolone colour coupler the photographic material which comprises in a layer thereof a compound of formula (1) is processed after exposure by a colour development process using a primary aromatic amine colour developing agent of known type. As usual in colour development processes the primary aromatic amine developing agent reduces the latent silver image to form a silver image and becomes oxidised, and the oxidised colour developer couples with the pyrazolone colour coupler of formula (1) to form reddish dye image.

After the colour development reaction to form the dye image the unexposed silver halide in the photographic material is removed using a silver halide solvent and the silver image is removed using a silver bleach bath. The silver halide and the silver may be removed by use of a single bleach-fix (blix) bath.

Suitable primary aromatic amine colour developing agents are p-phenylenediamine compounds, for example 4-amino-N, N-dimethylaniline hydrochloride, 4-amino-N,N-diethylaniline hydrochloride, 4-amino-3-methyl-N,N-diethylaniline hydrochlorine and p-aminophenol compounds for example a p-aminophenol itself and 2,6-dichloro-4-aminophenol.

The following Examples will serve to illustrate the invention (m.p. means melting point).

EXAMPLE 1

(a) 3-t-Butyl 1-(4'-nitrophenyl)pyrazolone 2-ene-5-ene

Ethyl pivaloyl acetate (4.55 g) and 4-nitrophenyl hydrazine (3.82 g) are fused at 130° C. and heated for 10 minutes. Acetic acid (5 ml) is added, and the whole heated for 2 hours. On cooling a solid forms. This is boilded out with ethanol (10 ml) to give 5.09 g of an orange solid (m.p. 146°–147° C.).

(b) 1-(4'-aminophenyl) 3-*t*-butylpyrazolone-2-ene-5-ene

The above nitro-pyrazolone is reduced under hydrogen and palladium/charcoal in 2-methoxyethanol (4.57 g in 150 ml), over 2½ hours. The solution is filtered through celite; evaporated to dryness, and boiled out with methanol (20 ml) to yield 2.43 g of a buff solid (m.p. 191°–195° C.)

(c) (Compound of the formula (2)

The above amino-pyrazolone (1.16 g) in pyridine (0.43 ml) and toluene (5 ml) is treated dropwise with a solution of 2,4-di-t-amylphenoxyacetic chloride (1.55 g) in toluene (5 ml). The mixture is heated under reflux for 3 hours, cooled and the toluene decanted off. The residue (a glass; 2.41 g) is taken up in ethyl acetate (5 ml) and, after filtering, cooled to −78° C. to give a solid; this is recrystallised from ethyl acetate to yield 2.0 g of a white solid (m. 82°–83° C.). The analytical sample is further crystallised from ethanol having then a melting point of 83° to 84° C.

EXAMPLE 2

Compound of the formula (3)

Ethyl pivaloyl acetate (0.86 g) and 3-hexadecylthiophenyl hydrazine (2.00 g) are heated at reflux in pyridine (0.39 g) and 2-methoxyethanol (25 ml) for 3 hours. On cooling a solid collected, which is recrystallised from ethanol to give 1.74 g of a cream powder (m.p. 61° to 52° C.).

EXAMPLE 3

Compound of the formula (5)

Ethyl adamantoyl acetate (6.59 g) and 4-methoxy phenyl hydrazine hydrochloride (4.6 g) are heated to reflux in acetic acid (50 ml) and ethanol (25 ml) with sodium acetate (2.2 g). On cooling, 5.4 g of a crystalline solid separates. This is recrystallised from ethanol (m.p. 185°–187° C.).

EXAMPLE 4

Compound of the formula (6)

3-Adamant-1-yl-1-1-(2,4,6-trichlorophenyl)pyrazol-id-2-ene-5-one: 2,4,6-Trichlorophenylhyrazine (4.23 g) is dissolved in glacial acetic acid and ethanol (100 ml), and ethyl adamantoyl acetate (5.01 g) is added. After 2 hours at room temperature water is added and the product collected and recrystallised from ethanol (m.p. 233°–234° C.

EXAMPLE 5

Compound of the formula (7)

(a)
3-t-Butyl-1-(2,6-dichloro-4-nitrophenyl)pyrazol-id-2-ene-5-one

Ethyl pivaloyl acetate (3.88 g) and 2,6-dichloro-4nitro phenyl hydrazine (5 g) are heated with ethanol (5 ml) and acetic acid (0.1 ml) for 3 days. On cooling a precipitate forms which is collected and identified by the nuclear magnetic resonance spectrum.

(b) 3-t-Butyl-1-2,6-dichloro-4-(2,4-di-t-amyl phenoxy acetyl amino) pyrazol-id-2-ene-5-one The above nitro compound is hydrogenated at room temperature in the presence of a hydrogenation catalyst (10% palladium on carbon) in ethanol. After uptake has ceased, the product is filtered free from catalyst, and the solvent evaporated. The oily product is dissolved in tetrahydrofuran (50 ml) and pyridine (2 ml). 2,4-di-t-amyl phenoxy acetyl chloride (2.7 g) is added. The mixture is heated to reflux for 5 hours. The product is cooled. Then dilute aqueous hydrochloric acid is added, and the product is extracted with ethyl acetate. The solution is dried and evaporated, and the product crystallises on triturating with methanol (m.p. 174°–179° C.).

EXAMPLE 6

A photographic coating is prepared on a photobase having the following coating weights

| | |
|---|---|
| Compound of the formula (2) | 4.5 mg/dm$^2$ |
| dissolved in tricresyl phosphate | 10 mg/dm$^2$ |
| together with a conventional silver photographic | |
| emulsion to give a silver coating weight of | 12 mg/dm$^2$; |
| all dispersed in gelatin | 23 mg/dm$^2$. |

The coatings are fogged with light, and then developed at 38° C. in a developing solution containing:

4-amino-3-methyl-N-ethyl-N-2-hydroxyethyl aniline sulphate (3.2 g), hydroxylamine sulphate (3 g), sodium carbonate (30 g), potassium bromide (1.8 g), potassium hydrogen sulphate (7 g), sodium bicarbonate (8 g), sodium sulphite (2 g) and sodium tripolyphosphate (2 g), made up to 1 liter.

The coatings are bleached and fixed, and the densities measured:

| Primary Adsorption | | Secondary Absorption | |
|---|---|---|---|
| maximum | density | maximum | density |
| 538 nm | 1.34 | 451 nm | 0.81 | that is to say the secondary density is 60% of the primary density.

Test coating prepared similarly with the following compounds give the following results:

| Compounds of the formula | Primary adsorption maximum | Secondary adsorption maximum | % Secondary density of primary density |
|---|---|---|---|
| (3) | 545 nm | 439 nm | 73 |
| (5) | 540 nm | 456 nm | 70 |
| (7) | 540 nm | 451 nm | 54 |

A control coating is prepared as above but using the known pyrazolone coupler of the formula

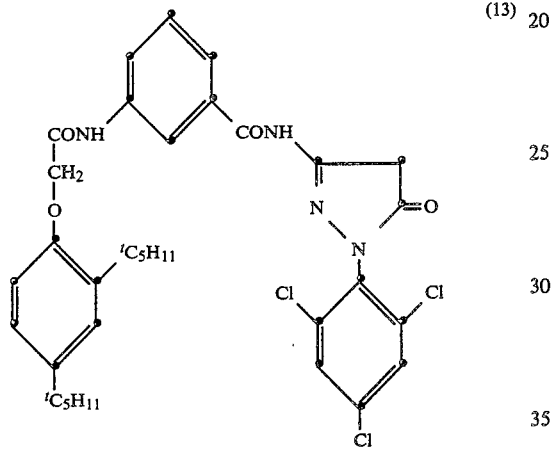
(13)

This has a primary adsorption maximum at 555 nm, a secondary absorption maximum at 434 nm and the secondary density is only 18% of the primary density.

What is claimed is:

1. Chromogenic, monochrome negative photographic material which comprises in at least one silver halide emulsion layer a pyrazolone compound having a high secondary absorption in the blue region of the visible spectrum, which is at least 54% of the primary absorption, said pyrazolone dye being of the formula

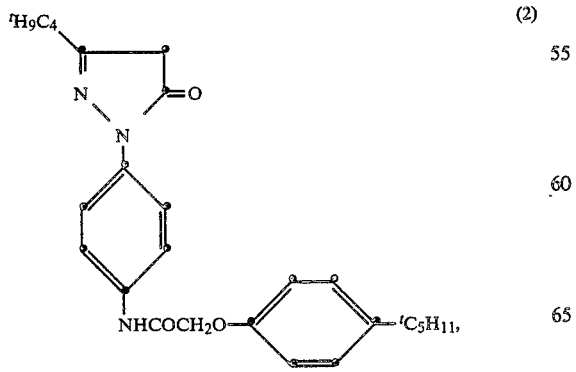
(2)

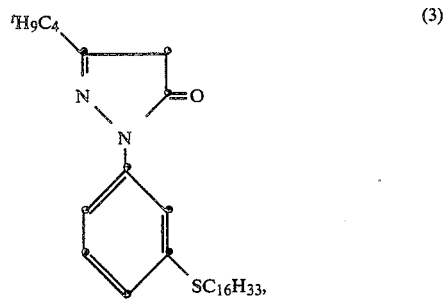
(3)

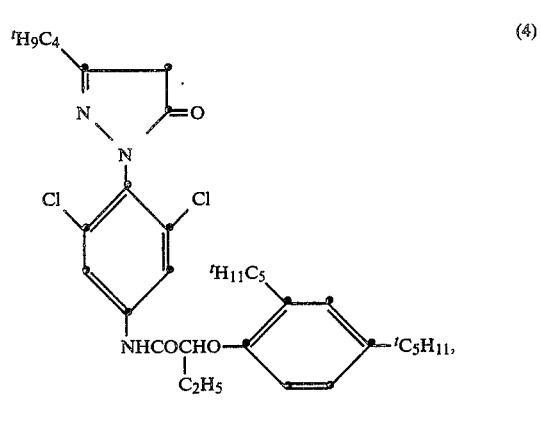
(4)

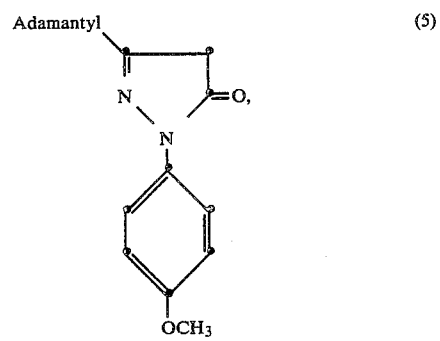
(5)

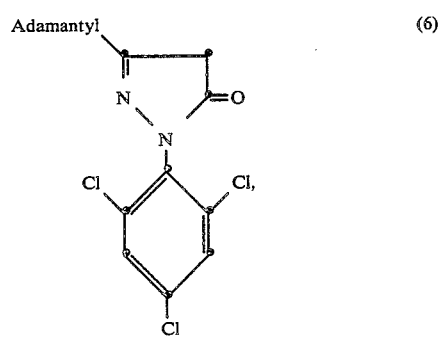
(6)

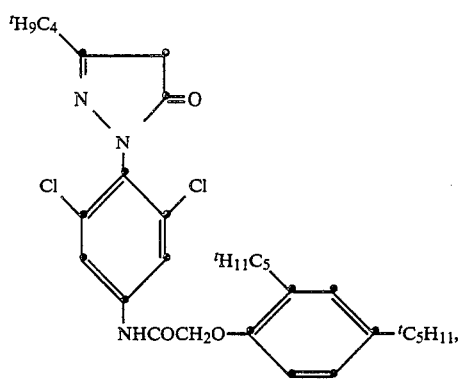
(7)
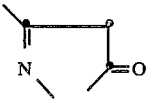
(9)
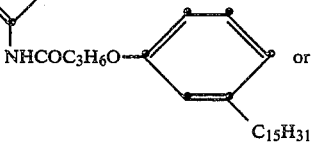
or
(8)
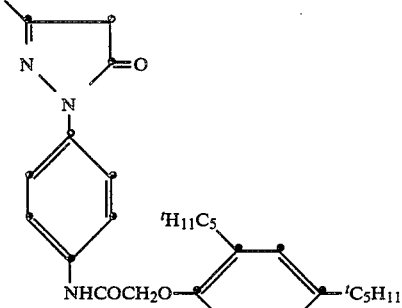
(10)
* * * * *